United States Patent [19]
Skladnev et al.

[11] Patent Number: 5,830,146
[45] Date of Patent: Nov. 3, 1998

[54] SHEATHED PROBES FOR TISSUE TYPE RECOGNITION

[75] Inventors: Victor N. Skladnev, Vaucluse; Richard L. Thompson, Killarneg Height, both of Australia; Irwin Wunderman, Mtn. View, Calif.

[73] Assignee: Polartechnics Limited, Sydney, Australia

[21] Appl. No.: 823,660

[22] Filed: Mar. 17, 1997

[51] Int. Cl.⁶ ............................................. A16B 1/00
[52] U.S. Cl. ..................... 600/478; 600/373; 600/121; 600/129
[58] Field of Search ................... 600/121, 124, 600/127, 129, 156, 157, 176, 177, 342, 372, 373, 473, 476, 431, 435, 478

[56] References Cited

U.S. PATENT DOCUMENTS

| | | | |
|---|---|---|---|
| 3,647,299 | 3/1972 | Lavallee | 356/41 |
| 3,910,701 | 10/1975 | Henderson et al. | 356/39 |
| 3,994,590 | 11/1976 | Di Martini et al. | 356/178 |
| 4,587,421 | 5/1986 | Robertson | 250/239 |
| 4,646,722 | 3/1987 | Silverstein et al. . | |
| 4,928,695 | 5/1990 | Goldman et al. . | |
| 4,942,877 | 7/1990 | Sakai et al. | 128/633 |
| 5,036,853 | 8/1991 | Jeffcoat et al. | 128/634 |
| 5,125,404 | 6/1992 | Kittrell et al. . | |
| 5,197,470 | 3/1993 | Helfer et al. . | |
| 5,329,935 | 7/1994 | Takahashi . | |
| 5,337,734 | 8/1994 | Saab . | |
| 5,361,762 | 11/1994 | Gunter . | |
| 5,398,685 | 3/1995 | Wilk et al. . | |
| 5,411,024 | 5/1995 | Thomas et al. | 128/634 |
| 5,423,320 | 6/1995 | Salzman et al. . | |
| 5,427,093 | 6/1995 | Ogawa et al. | 128/633 |
| 5,462,544 | 10/1995 | Saksena et al. | 600/15 |
| 5,520,177 | 5/1996 | Ogawa et al. . | |
| 5,536,236 | 7/1996 | Yabe et al. | 600/125 |
| 5,556,367 | 9/1996 | Yabe et al. | 600/124 |
| 5,573,494 | 11/1996 | Yabe et al. | 600/121 |
| 5,588,432 | 12/1996 | Crowley . | |
| 5,596,988 | 1/1997 | Markle et al. . | |
| 5,596,992 | 1/1997 | Haaland et al. . | |
| 5,632,717 | 5/1997 | Yoon | 600/106 |
| 5,651,767 | 7/1997 | Schulman et al. . | |
| 5,662,588 | 9/1997 | Lida | 600/121 |
| 5,674,181 | 10/1997 | Lida | 600/127 |
| 5,685,822 | 11/1997 | Harhen | 600/125 |
| 5,695,448 | 12/1997 | Kimura et al. | 600/121 |
| 5,695,449 | 12/1997 | Moriyama | 600/122 |
| 5,704,892 | 1/1998 | Adair | 600/121 |

OTHER PUBLICATIONS

Mendelson, Ph.D. et al., Design and Evaluation of a New Reflectance Pulse Oximeter Sensor, Medical Instrument, vol. 11, No. 4, pp. 187–173, 1988.

Neuman, M.R., In Medical Instrumentation: Application and Design, pp. 265–266, Webster, J.G. (ed) 2nd Ed. Boston: Houghton Miffliin, 1992.

*Primary Examiner*—Marvin M. Lateef
*Assistant Examiner*—Shawna J. Shaw
*Attorney, Agent, or Firm*—Gottlieb, Rackman & Reisman, P.C.

[57] ABSTRACT

The invention incorporates electrodes in the tip of the sheath cover for a diagnostic probe that makes both electric and optical measurements of tissue contacted by the sheath. The electrodes are positioned relative to the optical window in such a way as to ensure that sealing is not compromised by the presence of the electrodes. The electrodes are close by to ensure that both the optical and electrical measurements are made on the same area of tissue. The invention uses the hoop tension in the sheath to apply the needed spring force to the electrode contact. In addition the invention provides a piece of turbid material such as a polymer of controlled composition as a built-in calibrator attached to the outside of the tip of the sheath.

16 Claims, 10 Drawing Sheets

SHEATHED PROBES FOR TISSUE TYPE RECOGNITION

FIELD OF THE INVENTION

This invention is a sheath intended for the recognition of tissue types and in particular for the detection of cervical precancer and cancer for use with a probe that performs both optical and electrical measurements while it is scanned over the surface of tissue, e.g. the cervix, and from these measurements makes a diagnosis of the health of the tissue.

BACKGROUND OF THE INVENTION

The medical profession often needs to have an objective assessment of the health of the tissue of a patient. The patient may have suffered tissue damage as a result of accidental or deliberate trauma as for example during a surgical operation. The patient may also be suffering some other more persistent irritation as a result, for example, of being confined to bed which can lead to bed sores. It is valuable for a medical practitioner to be able to tell in advance the type of treatment that would benefit the patient.

It is well known, for example, that early detection of tissues displaying pre-cancer or cancer modifications is important for successful medical treatment. We have already disclosed an apparatus and method for carrying out this detection in patent application Ser. No. 08/332,830, assigned to the same assignee as the current invention.

Between uses probes can be disinfected by soaking in a suitable solution. For many patients this procedure is not acceptable. They require that the probe has not previously been used on other patients for fear of cross-contamination and infection. This requirement can be achieved by equipping the probe with a discardable, sterile sheath. Such an assembly must ensure that no part of the probe which is used on a patient could have come in contact with a previous patient. Sheaths that have been designed for other types of probes lack features that would make them suitable for use on a probe that performs both optical and electrical measurements while it is scanned over the surface of the cervix. For example ultrasonic probe sheaths would not be suitable. In particular they do not have provision to make simultaneous optical and electrical measurements. The particular difficulties that have been overcome by this invention arise from the fact that both electrical and optical measurements are to be performed on the same area of tissue. It is therefore not feasible to install a simple sheath such as a condom over the tip of the probe. Such a sheath may, for example, enable some optical measurements to be made but would prevent electrical contact being made with the tissue with the optically transparent cover in place.

SUMMARY OF THE INVENTION

This difficulty is overcome in the present invention by incorporating electrodes in the tip of the sheath. They are positioned relative to the optical window in such a way as to ensure that sealing of the sheath against the probe is not compromised by the presence of the electrodes. The electrodes are close to the optical window to ensure that both the optical and electrical measurements are made on the same area of tissue.

A further difficultly that is overcome by this invention is the requirement that electrical contact is made in a reliable manner between the internal probe electrical connections and the electrodes in the sheath. Any failure of these connections during probing could lead to false readings with serious consequences to the patient. Because the optical window has to be relatively thin and the electrodes are nearby, pressure exerted by a spring contact on the electrode has the potential to break the seal between the electrode and the window. The special configuration used in this invention avoids this danger by using the hoop tension in the sheath to apply the needed spring force to the electrode contact.

In addition the invention provides a built-in calibrator. This is achieved by attaching to the outside of the tip of the sheath a piece of turbid material such as a polymer of controlled composition. This material acts in the manner of the tissue to be measured in that it backscatters the light from the probe tip to a controlled degree. This enables the probe's computer to check the overall performance of the optical system thereby verifying that the probe and its sheath are performing optically according to specifications and that the sheath has been correctly fitted. The piece of turbid material is removed prior to using the probe on a patient.

DETAILED DESCRIPTION OF PREFERRED EMBODIMENTS

The sheath of the present invention does not hinder the reading of the optical and electrical properties of the tissue being determined at effectively the same place. Where more than one electrode is employed, the electrodes are essentially symmetrically positioned relative to the optical system.

The optical system for the probe may take one of several forms. The probe may employ hybrid opto-electronic systems that place the opto-electronics components at the tip of the probe or employ fibre optics for delivering the optical signal to and from the tissue. The invention is described for application to probes built by both methods.

A detailed description of hybrid probes is contained in our copending application filed this same date entitled "Hybrid Probe For Tissue Type Recognition", which is included herein by reference. As explained in that application, a hybrid probe is distinguished by the avoidance of the use of optical fibers to convey illumination to and/or from the active portion of the probe. It is designed to examine areas of tissue having a diameter of the order of 2 mm, which requires that photodiode detectors be placed in close juxtaposition with light emitters yet optically isolated so that light signals do not pass directly from an emitter to a detector without intervention (i.e. backscattering) by the tissue under examination. This is accomplished in the hybrid probe by the use of metal barriers. The metal barriers also shield the detector circuitry from electrical interference carried by current pulses that must be applied to the LEDs to induce them to emit light to illuminate the portion of the tissue being tested. The metal barrier may be left floating or grounded, but can also serve an additional role as an electrode for making electrical measurements to replace or supplement the two or three noble metal electrodes adjacent to the hybrid circuit normally used for the electrical measurements to be made on the tissue.

In addition the hybrid structure has a preamplifier in close proximity to the photodiodes to amplify the small current from the photodiode detectors and feed it to the electronics in the handle of the probe and from there to the analysis circuitry.

Probes using optical fibers are temperature sensitive. This temperature sensitivity often occurs at bends in the fiber. It is often not practical to measure these temperatures so compensation is difficult to achieve. A change in temperature at the tip of the probe is likely to occur when the probe is brought into contact with the tissue of a warm blooded being. The hybrid probe overcomes the forms of temperature sensitivity arising from the fibers. The radiation output of LEDs is also temperature sensitive but for precise measurements can be compensated by using a characteristic of the LED to determine its own temperature. The bandgap potential of LEDs is a known function of temperature, allowing the temperature to be determined by applying a known current to the diode and measuring the potential across it. This can then be used to correct for the output of the LED using established equations thereby compensating for the changed radiation emission caused by temperature changes. Further details are provided in the accompanying application mentioned above.

Figure 1A:
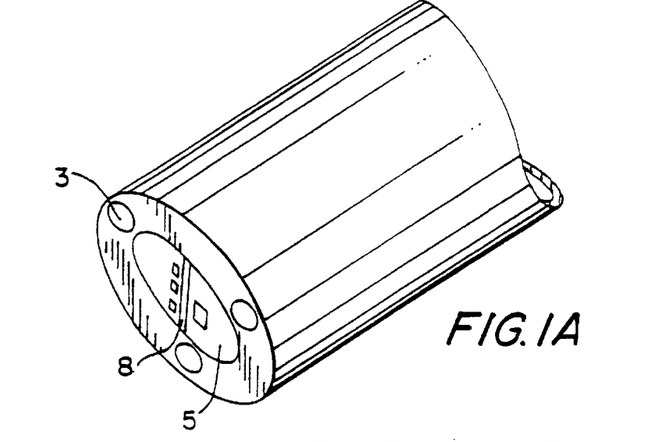
FIG. 1 is an illustration, partly in section, of a sheath fitted to a hybrid type probe.
Figure 1B:
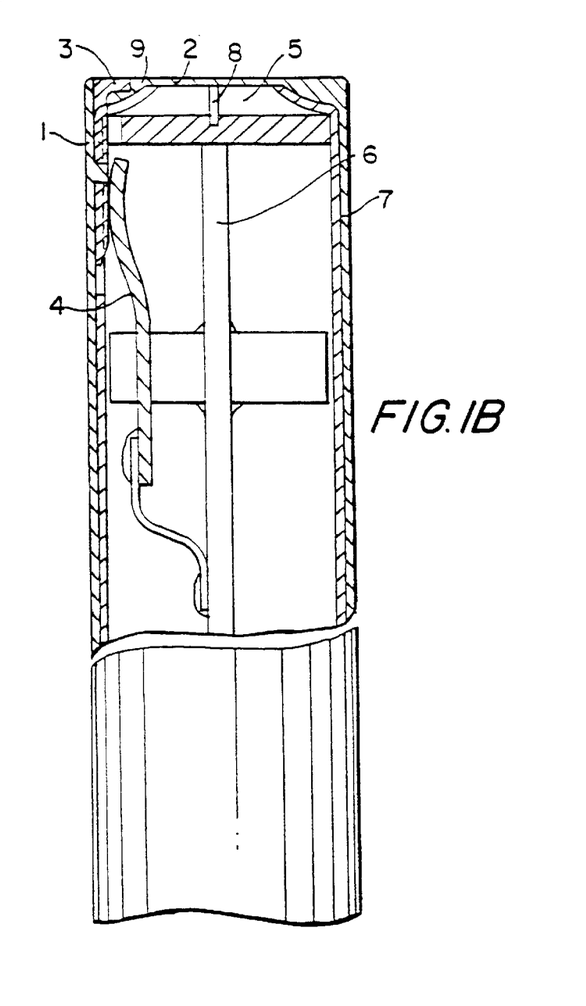

FIG. 1 shows how the invention is applied to a hybrid probe. The exterior sheath body 1 includes a thin transparent window 2 at its tip so that the optical measurements can be made. Adjacent to the window is shown one of the electrodes 3 used for making the electrical measurements. Electrical contact from the inner probe assembly is made via contact 4. The hybrid opto-electronics is situated in the area 5. Electrical signals to and from the opto-electronics are handled by the printed circuit board 6.

The main body of the probe is contained within the electrostatic shield 7.

The thickness of window 2 is constrained by the optical system. It is related to the thickness of the optical barrier 8. It is important that light from the emitting side of the hybrid assembly 5 cannot simply reflect off the outer surface of the window 2 back into the detecting side of the hybrid. If this occurs, the diagnostic ability of the device will be compromised. The light must travel via the tissue being measured. The relationship between the window thickness and the barrier thickness can be determined geometrically by projecting the light from the emitters on the radiation source side of the area 5 past the edge of the barrier and onto the upper surface of the window. This light will reflect back at an equal angle and the barrier must be wide enough to prevent the light reflected from the upper surface of the window from reaching the detector side of the area 5. The light must pass via the tissue where it can assist with the diagnosis.

The thickness of the barrier is in turn constrained by the need to maintain adequate optical efficiency. A thick barrier necessitates that the light travels a long way between the emitters and the detector and is attenuated as it travels. To avoid having to make the barrier excessively thick the window 2 needs to be kept thin.

Since the optical measurements may have to be made at high precision, the optical couplings between the components of the system need to be reliable. To this end the inside of the sheath tip is wetted with a suitable liquid so that the optical coupling is enhanced. The liquid employed should not be volatile and may for example be a mineral oil. Alternatively glycerine may be used which has the advantage of being water-soluble and non-irritating to normal tissue should it come in contact with the operator's or patient's skin. A thixotropic mixture may also be employed, for example a dentifrice gel, particularly a pediatric gel or an optically clear hand cleaning gel. In this invention the gel at the tip of the sheath will spread over the end window as the probe presses on it.

Figure 10:
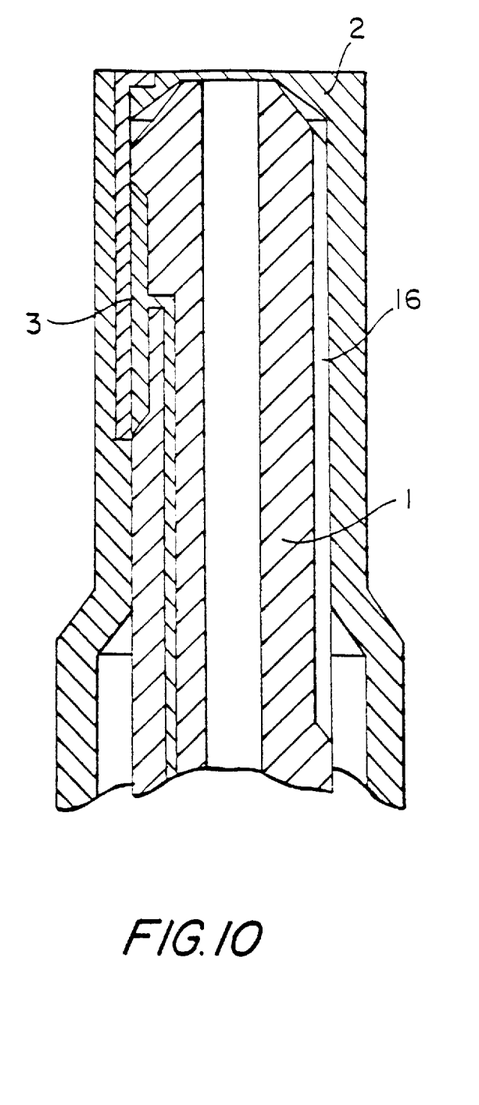
FIG. 10 is an illustration in section of a groove in the probe.

During the process of fitting the sheath to the probe, air and excess liquid will need to escape. It is important therefore to include a groove in the body of the probe so that this can occur. FIG. 10 illustrates how a groove 16 can be incorporated into a probe.

Orientation is also important. The electrodes must line up with their corresponding contacts on the probe body. To this end the probe body and the sheath are fitted with guides that constrain the sheath to line up with the electrical contacts. Spiral grooves or various probe and sheath shapes such as a triangular cross-section can be employed for this purpose.

A particularly critical feature of the embodiment illustrated in FIG. 1 is the region 9 on the tip of the sheath. This is a potential point of weakness that could endanger the patient unless the features illustrated are included. It will be noted that the window 2 does not extend across to the electrode 3 but passes under the electrode. This feature provides the necessary strength and path length to avoid fracture of the join between the plastic used to make the window and the metal electrode. Should this join open, body fluids could enter and contaminate the probe body. Similar failure of another sheath could then lead to these contaminants leaving the probe and reaching a subsequent patient.

Figure 2A:
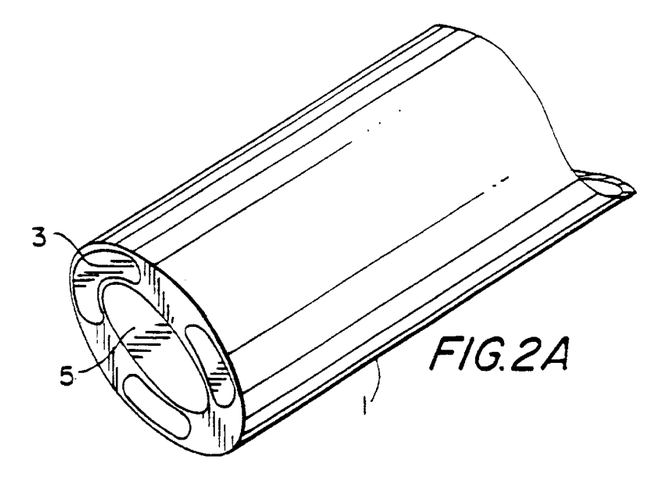
FIG. 2 is an illustration, partly in section, of the sheath alone.
Figure 2B:
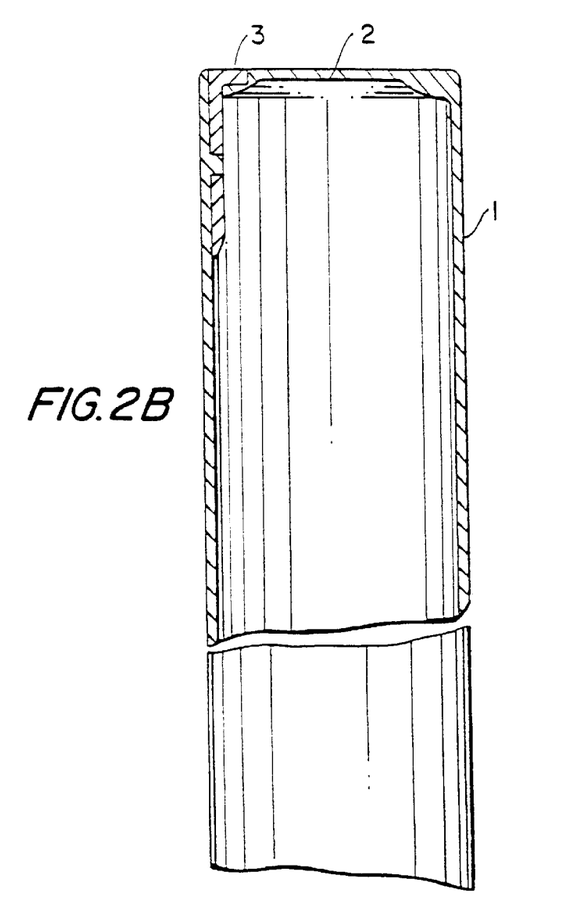

FIG. 2 shows the sheath without the probe present. The end view shows that kidney-shaped electrodes 3 can be used. These have the advantage of providing a larger surface area without interfering with the optical measurements. Larger electrodes by their nature produce less noisy data because they are sampling a larger area of tissue which is naturally less variable than a smaller area.

Figure 3:
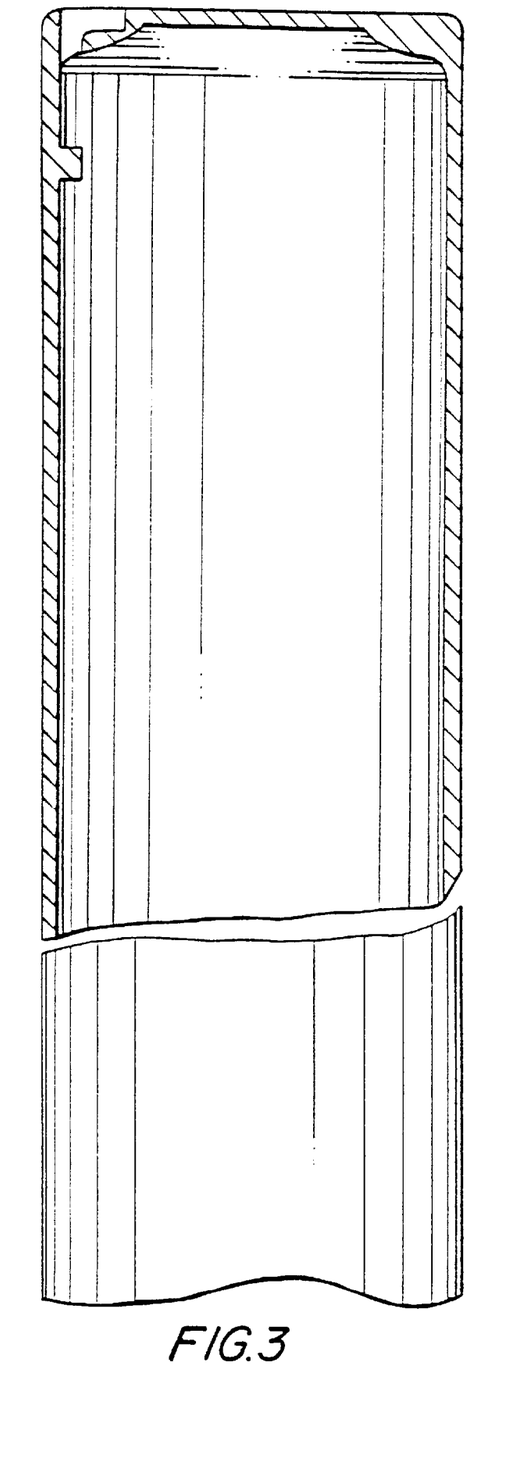
FIG. 3 is an illustration in section of the sheath alone without electrodes fitted.
Figure 4A:
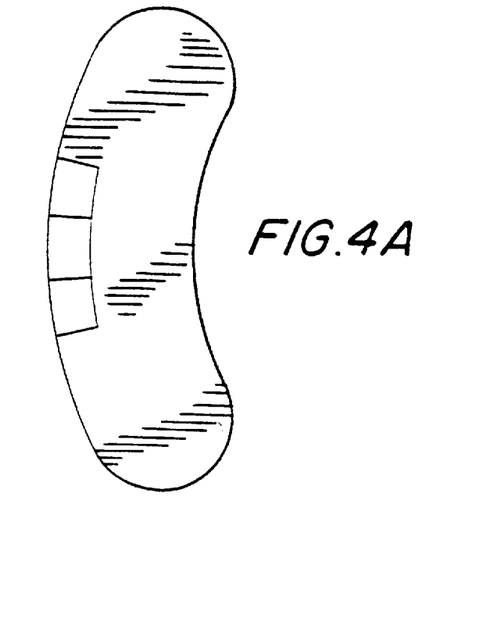
FIG. 4 is an illustration of one form of an electrode capable of being fitted to the sheath of FIG. 3.
Figure 4B:
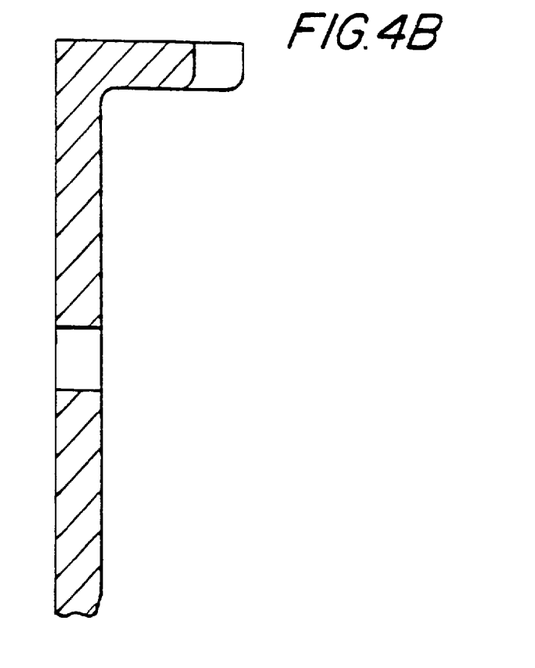
Figure 5:
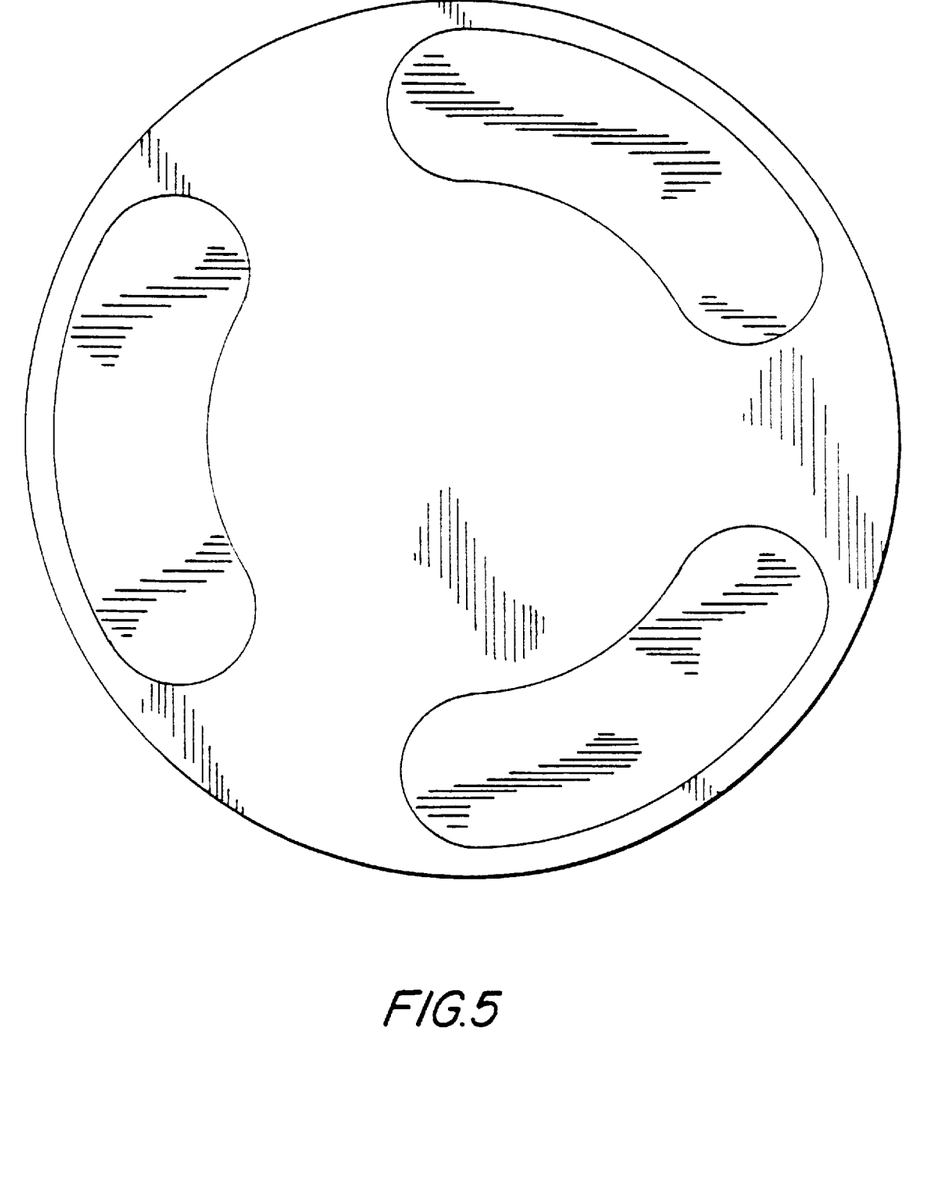
FIG. 5 is an end view of the sheath with electrodes fitted.
Figure 6A:
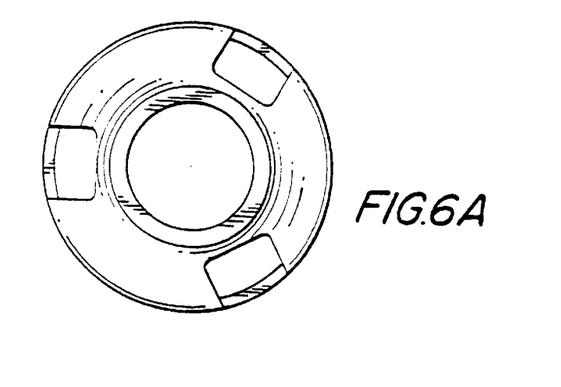
FIG. 6 is an illustration, partly in section, of the hybrid probe without a sheath.
Figure 6B:
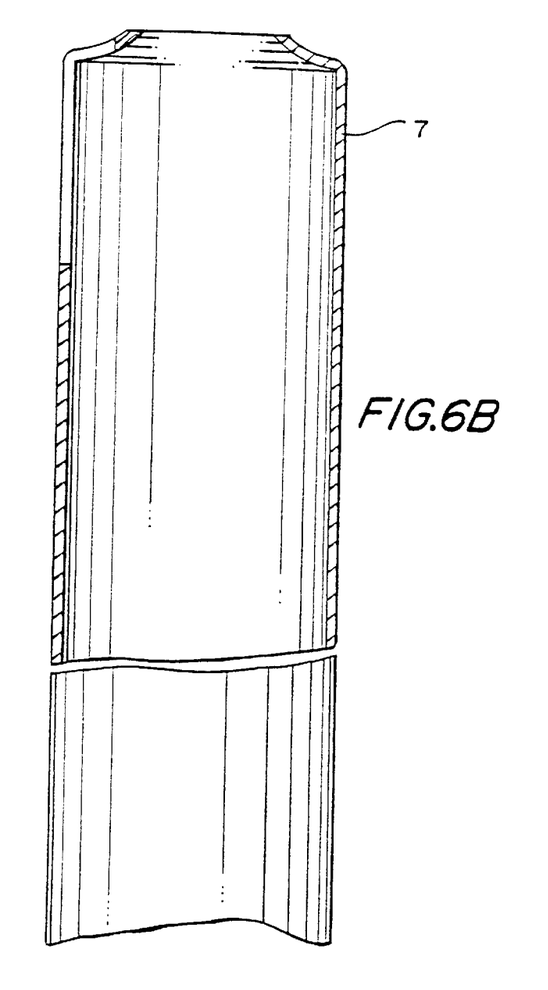

FIG. 3 shows the sheath without electrodes fitted to indicate the form of plastic molding that could be used to make the sheath. Electrodes of the form shown in FIG. 4 would be fitted to this molding. An end view of the resulting sheath is shown in FIG. 5. FIG. 6 indicates the type of probe that is suited to the sheath described above.

Figure 7A:
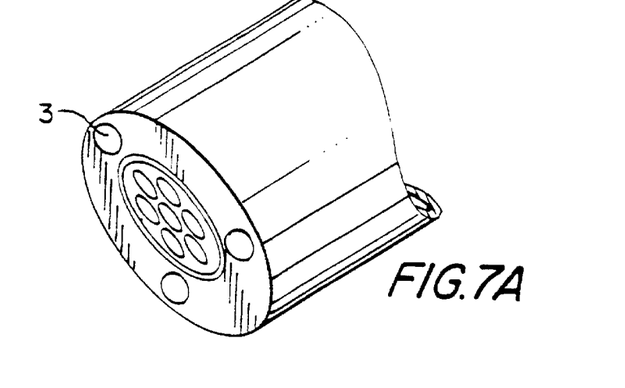
FIG. 7 is an illustration, partly in section, of a sheath fitted to a fibre type probe.
Figure 7B:
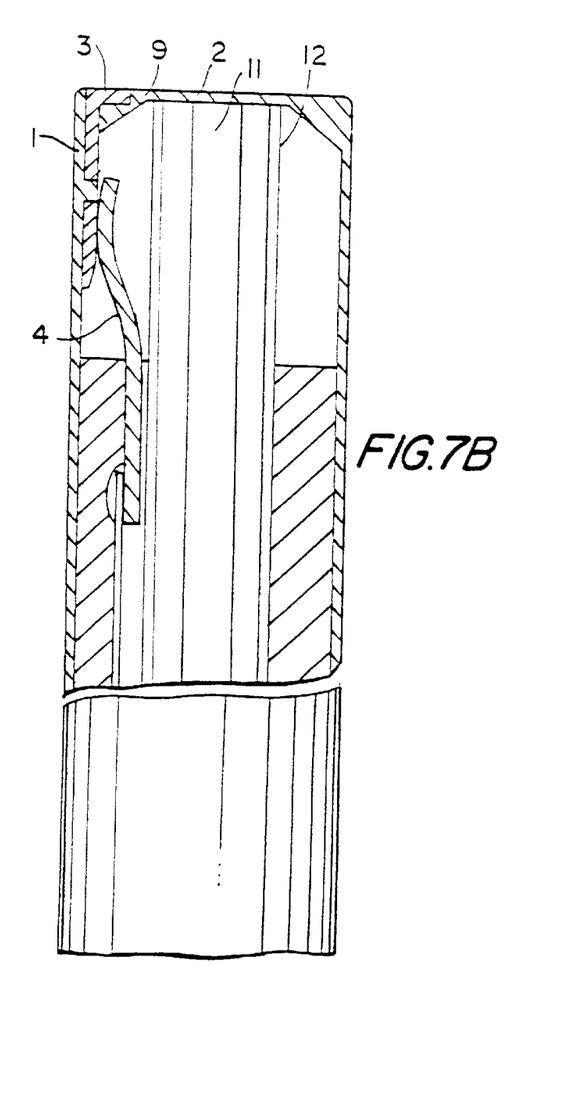

FIG. 7 shows the sheath fitted to a probe employing optical fibers to convey light to and from the tissue surface. Such a probe is disclosed in our copending patent application Ser. No. 08/332,830, assigned to the present assignee. The component parts are similar to those described above, with a major difference being that the opto-electronics section is replaced by fibers 11 held within a casing 12. In this embodiment the window needs to be thinner than in previously described embodiments since the fibers delivering the radiation to the tissue are adjacent to the detector fiber. Since the performance of the device is adversely affected by radiation leaking directly from the emitter to the detector, the window needs to be of the order of 0.2 millimeter to avoid this problem.

Figure 8A:
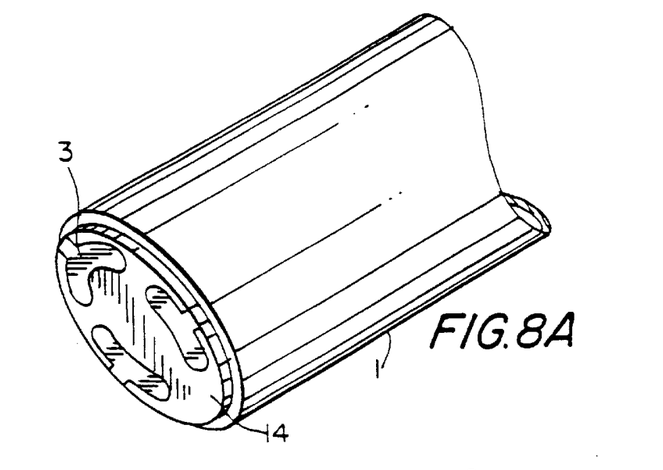
FIG. 8 is an illustration, partly in section, of another embodiment of the invention.
Figure 8B:
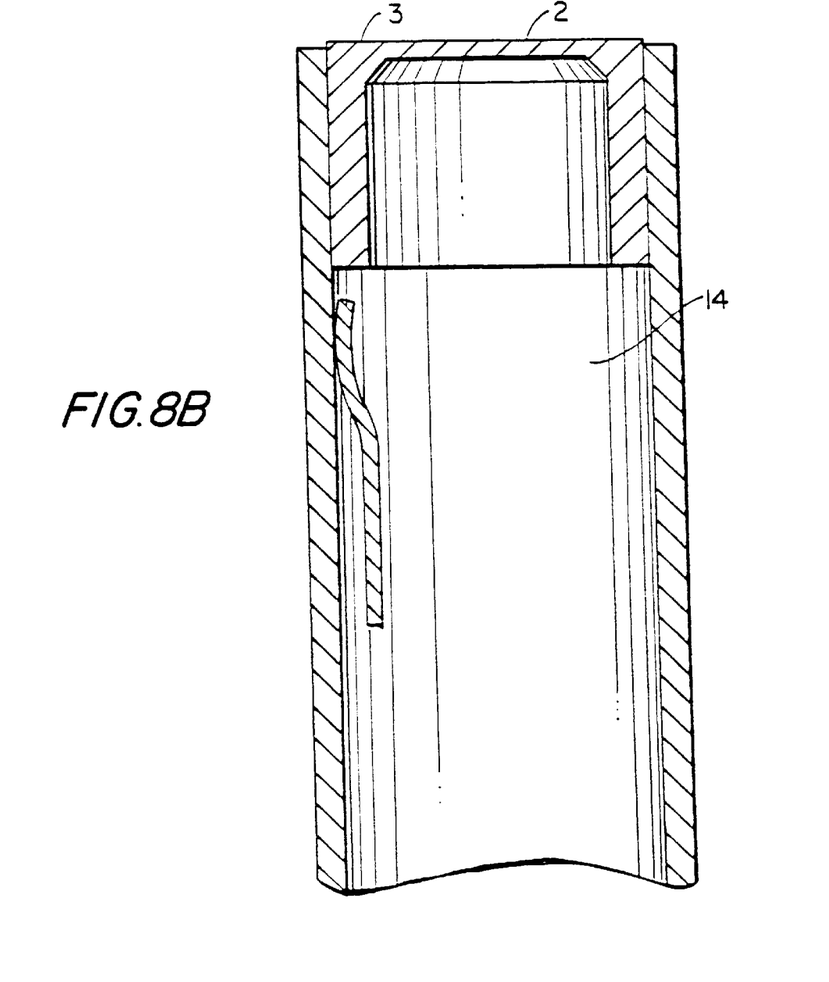

FIG. 8 is another embodiment of the invention. In this case the electrodes 3 are printed on the surface of the window 2 and extend down the wall of the cup 14 that forms the tip of the probe. Electrical contact is achieved by coating the inside of the tube 1 with an electrical conductor 15. The electrical contacts 4 on the probe engages this coating and completes the circuit from the inside of the sheath to the electrodes 3 on the front window 2.

Figure 9:
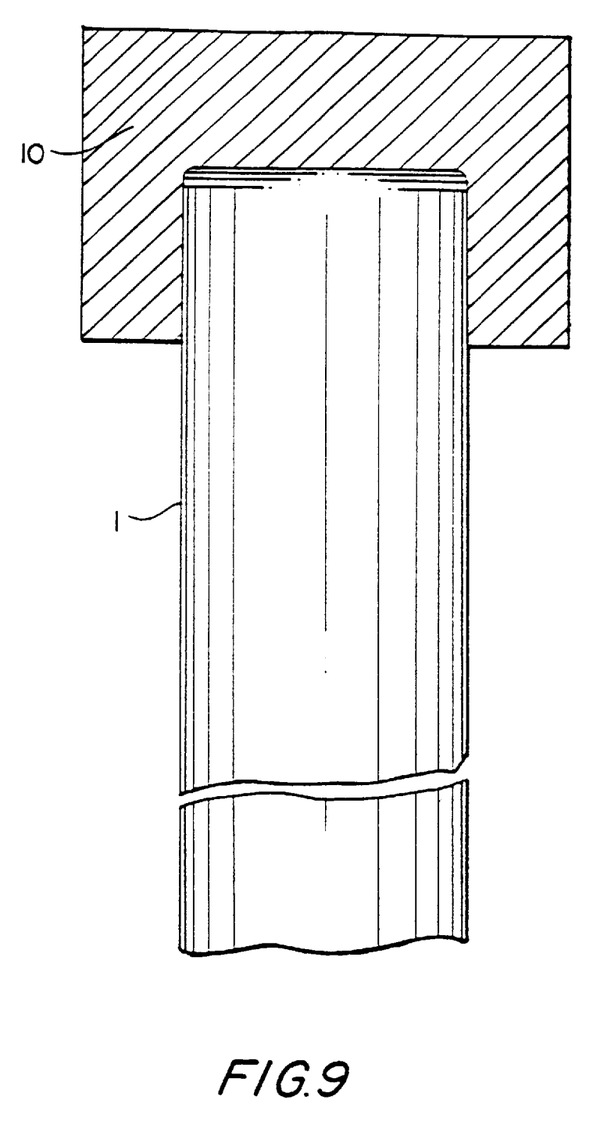
FIG. 9 is an illustration, partly in section, of a turbid calibrator fitted to the tip of a sheath.

FIG. 9 shows how a turbid calibrator 10 is fitted to the sheath. Calibrators are described in greater detail in a copending application filed this date entitled "Apparatus For Checking The Calibration Of Optical Probes", whose disclosure is incorporated herein by reference. As explained in that application, a probe may be calibrated by simply pressing the tip against a block of material of controlled characteristics. In this form of calibrator a transparent elastomer is used into which has been incorporated a light-scattering material. The light-scattering material can be any one of a number of whiteners such as titanium dioxide, barium sulphate, or magnesium oxide. The concentration of whitener is varied to suit the particular turbidity that is needed. The elastomer can be, for example, a polyurethane rubber or a silicone rubber.

Elastomer calibrators may be assembled on the tip with the other components of the sheath and is removed after calibrating the system and before the probe is put into use.

Another form of calibrator comprises a turbid elastomer on the face of which is placed a film of flexible polymer which is intended to simulate the structure of the material that is to be measured. The latter may for example be a layer of precancerous cells on cervical tissue. The layer of polymer film that is placed over the elastomer should have optical characteristics analogous to the material to be detected by the probe. In the case of cervical intra-epithelial neoplasia, the cervical tissue becomes covered with a layer of abnormal cells. A calibrator intended to check the performance of a device that is to detect this layer of cells may provide more reliable diagnoses if it is calibrated in an environment equivalent to that pertaining during the diagnostic probing, that is, by using a layered calibrator.

A liquid film may be included between the tip of the sheath 1 and the piece of turbid material to ensure that the optical coupling is reliable. Immediately prior to using the probe the operator advises the controller to perform a calibration check. The controller is typically programmed to refuse to function unless the calibration check is passed. The turbid calibrator 10 is then removed from the sheath exposing the face for application to the tissue to be examined. By performing these operations the danger of making erroneous measurements because the sheath is incorrectly fitted are avoided.

Provision has been made to ensure that the sheath is firmly secured in place after it has been fitted to the probe. This is achieved by arranging for a part of the sheath to be of smaller diameter than the probe and for a corresponding indentation to be present in the probe so that the sheath slips into that indentation thereby locking the sheath in place and providing a force which keeps the optical and electrical contacts secure while the probe is in use. A locking ring may also be employed. The locking devices are not illustrated.

Although the invention has been described in terms of preferred embodiments its full scope is not so limited. Accordingly the invention is defined by the proper legal scope of the following claims.

What is claimed is:

1. A sheathed probe having an active tip for medical diagnosis comprising a sheath and a probe, said sheath being removable from said probe and replaceable with another identical sheath upon said probe to prevent cross contamination between patients, said sheath comprising an optically transparent area at the active tip of the sheath, one or more electrodes at the active tip of the sheath adjacent to said optically transparent area, wherein electrical and optical measurements may be made simultaneously by the sheathed probe on an area of tissue wherein the probe comprises electrical contacts, said sheath is cylindrical and has a hoop tension, and said hoop tension forces a reliable electrical contact between said one or more electrodes on the tip of the sheath and corresponding said electrical contacts on the probe.

2. A sheathed probe as claimed in claim 1 wherein said sheath has a thin transparent window to pass radiation to and from optical elements of the probe.

3. A sheathed probe having an active tip for medical diagnosis comprising a sheath and a probe, said sheath being removable from the probe and replaceable with another identical sheath upon said probe to prevent cross contamination between patients said sheath comprising an optically transparent area at the active tip of the sheath, one or more electrodes at the active top of the sheath adjacent to said optically transparent area, wherein electrical and optical measurements may be made simultaneously by the sheathed probe on an area of tissue, wherein said sheath has a thin transparent window at the active tip of the sheath to pass radiation to and from optical elements of the probe, and wherein said window is constructed to pass under said one or more electrodes.

4. A sheathed probe as claimed in claim 1 wherein said sheath has an inside wetted with a liquid that enhances optical coupling.

5. A sheathed probe as claimed in claim 4 wherein said optical liquid comprises mineral oil or glycerine.

6. A sheathed probe as claimed in claim 5 wherein said optical liquid is thixotropic.

7. A sheathed probe as claimed in claim 1 comprising a turbid material at the tip of the sheath which serves the purpose of checking the calibration of the probe and the precision of the optical coupling to the optically transparent area and wherein said turbid material can be removed prior to using the probe on a patient.

8. A sheathed probe having an active tip for medical diagnosis comprising a sheath and a probe, said sheath being removable from the probe and replaceable with another identical sheath upon said probe to prevent cross contamination between patients said sheath comprising an optically transparent area at the active tip of the sheath, and one or more electrodes at the active tip of the sheath adjacent to said optically transparent area, wherein electrical and optical measurements may be made simultaneously by the sheathed probe on an area of tissue, said sheath employing kidney-shaped electrodes to achieve a large area of electrode within the confines of the optical and other constraints.

9. A sheathed probe as claimed in claim 1 that is equipped with a longitudinal groove which allows entrapped air and excess liquid to escape when said sheath is slid over the probe.

10. A sheathed probe as claimed in claim 1 having electrical contacts on a surface of the probe and shaped to ensure that a sheath takes up a suitable orientation when mated with the probe, wherein said electrical contacts on the surface of the probe line up with corresponding contacts on the inside of the sheath.

11. An apparatus as claimed in claim 3 wherein said sheath has an inside wetted with a liquid that enhances optical coupling.

12. An apparatus as claimed in claim 3 comprising a turbid material at the tip of the sheath which serves the purpose of checking the calibration of the probe and the precision of the optical coupling to the optically transparent area and wherein said turbid material can be removed prior to using the probe on a patient.

13. A sheathed probe as claimed in claim 3 that is equipped with a longitudinal groove which allows entrapped air and excess liquid to escape when said sheath is slid over the probe.

14. A sheathed probe as claimed in claim 8 that is equipped with a longitudinal groove which allows entrapped air and excess liquid to escape when said sheath is slid over the probe.

15. A sheathed probe as claimed in claim of claim 3 having electrical contacts on a surface of the probe and shaped to ensure that a sheath takes up a suitable orientation when mated with the probe, wherein said electrical contacts on the surface of the probe line up with corresponding contacts on the inside of the sheath.

16. A sheathed probe as claimed in claim 8 having electrical contacts on a surface of the probe and shaped to ensure that a sheath takes up a suitable orientation when mated with the probe, wherein said electrical contacts on the surface of the probe line up with corresponding contacts on the inside of the sheath.

* * * * *